(12) United States Patent
Sambanthamurthi et al.

(10) Patent No.: US 8,309,145 B2
(45) Date of Patent: *Nov. 13, 2012

(54) TREATMENT OF VEGETATION LIQUORS DERIVED FROM OIL-BEARING FRUIT

(75) Inventors: Ravigadevi Sambanthamurthi, Selangor (MY); Yew Ai Tan, Kuala Lumpur (MY); Kalyana Sundram, Selangor (MY)

(73) Assignee: Malaysian Palm Oil Board, Selangor (MY)

( * ) Notice: Subject to any disclaimer, the term of this patent is extended or adjusted under 35 U.S.C. 154(b) by 357 days.

This patent is subject to a terminal disclaimer.

(21) Appl. No.: 12/126,736

(22) Filed: May 23, 2008

(65) Prior Publication Data

US 2009/0053333 A1    Feb. 26, 2009

Related U.S. Application Data

(60) Continuation of application No. 10/269,224, filed on Oct. 11, 2002, now Pat. No. 7,387,802, which is a division of application No. 09/405,206, filed on Sep. 24, 1999, now abandoned.

(30) Foreign Application Priority Data

Sep. 24, 1998 (MY) ................................ PI 9804378

(51) Int. Cl.
*A61K 36/889* (2006.01)
(52) U.S. Cl. ......... 424/777; 424/725; 424/727; 210/650
(58) Field of Classification Search .................. None
See application file for complete search history.

(56) References Cited

U.S. PATENT DOCUMENTS

| | | | |
|---|---|---|---|
| 4,533,501 A | 8/1985 | Sen Gupta | |
| 4,613,672 A | 9/1986 | Hara | |
| 5,998,641 A | 12/1999 | Ganguli et al. | |
| 7,387,802 B2 * | 6/2008 | Sambanthamurthi et al. | 424/727 |

FOREIGN PATENT DOCUMENTS

WO    WO 92/11206    7/1992

OTHER PUBLICATIONS

Ngan et al., A novel treatment process for palm oil mill effluent, PORIM Technology No. 19, Oct. 1996.
Nor et al., Palm oil mill effluent treatment by ultrafiltration: An economic analysis, Second Asean Workshop on Membrane Technology, 1992.
Phang, Advances in Limonology (1987), vol. 28, pp. 77-94).
U.S. Notice of Allowance and Fee(s) Due for U.S. Appl. No. 10/269,224 dated Feb. 19, 2009.
U.S. Office Action for U.S. Appl. No. 10/269,224 dated Jun. 26, 2007.
U.S. Advisory Action for U.S. Appl. No. 10/269,224 dated Apr. 10, 2007.
U.S. Office Action for U.S. Appl. No. 10/269,224 dated Oct. 10, 2006.
U.S. Office Action for U.S. Appl. No. 10/269,224 dated Aug. 30, 2005.

* cited by examiner

*Primary Examiner* — Susan Hoffman
(74) *Attorney, Agent, or Firm* — Foley & Lardner LLP

(57) ABSTRACT

The present invention relates to processes for the treatment of liquors derived from oil-bearing fruit, for example from oil palm fruit, and to products therefrom. Typically a process involves removal of undissolved solids, oleaginous parts, colloids and higher weight molecules from the vegetation liquor to give an aqueous fraction containing phytochemicals, for example, flavonoids, phenolic acids and hydroxy acids. Subsequently, pH adjustment and solvent extraction upon said aqueous fraction realise an extract rich in hydroxy acids or phenolic acids or flavonoids or any combination thereof. Applications of the substances subject of this invention are to be found in drinks, edible products, tonics, health supplements, antioxidant additives, cosmetics, soaps, shampoos, detergents, drugs or medicinal products.

17 Claims, No Drawings

US 8,309,145 B2

TREATMENT OF VEGETATION LIQUORS DERIVED FROM OIL-BEARING FRUIT

This application is a continuation of U.S. patent application Ser. No. 10/269,224, filed Oct. 11, 2002, now U.S. Pat. No. 7,387,802, which is a divisional of U.S. patent application Ser. No. 09/405,206, filed Sep. 24, 1999, now abandoned, which claims the benefit of Malaysian Patent Application No. PI 9804378, filed Sep. 24, 1998, each of which are incorporated herein by reference in their entirety including all figures and tables.

Throughout this application, various publications are referenced. These publications are incorporated herein by reference to describe more fully the state of the art to which the invention pertains.

TECHNICAL FIELD

The present invention relates to processes for the treatment of vegetation liquors derived from oil-bearing fruit, for example from oil palm fruit, and to products therefrom.

BACKGROUND ART

Vegetation liquors are obtainable, among other ways, either directly from plants for the purpose of extracting useful components or as a waste stream in the processing of plant material which is often the cause of environmental pollution leading to the degradation of waterways and sources of water. In this invention, the vegetation liquors derived from oil-bearing fruit may be obtained from or using one of the following:
  a) oil-bearing fruit of any herbaceous or arboraceous plant or from a combination of such fruit,
  b) fruit of the oil palm plant,
  c) waste streams from oil mills that process oil-bearing fruit,
  d) palm oil mill effluent or concentrated palm oil mill effluent,
  e) steriliser condensate from a palm oil mill,
  f) waste from any oil clarification stage at a palm oil mill,
  g) waste from any centrifuge stage at a palm oil mill, or
  h) waste from any oil trap at a palm oil mill.

The above list is not intended to exhaust the possible sources of vegetation liquors derived from oil-bearing fruit and any other such sources not named explicitly, for example, olive flume wastewater, are meant to be included as input material for the invention. It will be clear that the input material is not restricted to pure fruit but also includes any ancillary vegetative matter collaterally processed with the fruit.

In the case of oil palm fruit processing, the extraction of palm oil generates a waste stream of vegetation liquor at more than twice the tonnage of the crude palm oil production. Currently there are several treatments and uses for vegetation liquors like palm oil mill effluent. Among them are either applying said effluent, with or without treatment, onto the crop growing area, or reduction of chemical and biological oxygen demand before release of treated effluent into the environment, or generation of feed for livestock, or generation of substrates for the growth of micro-organisms ("A novel treatment process for palm oil mill effluent", Ma Ah Ngan et al, *PORIM Technology* No. 19, October 1996). The use of membrane filtration in the treatment of such effluents, whether in research or in practice, has hitherto been focussed upon one or more of the above objectives rather than those aims which are the subject of this invention ("Palm oil mill effluent treatment by ultrafiltration: An economic analysis", Mohd. Tusirin Nor et al, Second Asean Workshop on membrane technology, 1982). However, existing treatments have not really provided a solution to the effluent problem, and proposed solutions do not seem to have been widely adopted perhaps because of adverse economics.

Furthermore, it has hitherto been accepted palm oil mill practice that the recovery of any remaining oil from effluent is not carried out despite the presence in said effluent of nominally one to two percent oil content, often more in reality. Similarly, palm oil mill effluent has hitherto been ignored as a potential source of water-soluble biologically active compounds including, but not limited to, flavonoids, phenolic acids and hydroxy acids. Neither has the oil palm fruit been used as a source for such compounds nor as a source of a drink or tonic based upon its aqueous part.

SUMMARY OF THE INVENTION

As stated in the preceding section, in this invention, the vegetation liquors derived from oil-bearing fruit may be obtained from or using one of the following:
  a) oil-bearing fruit of any herbaceous or arboraceous plant or from a combination of such fruit,
  b) fruit of the oil palm plant,
  c) waste streams from oil mills that process oil-bearing fruit,
  d) palm oil mill effluent or concentrated palm oil mill effluent,
  e) steriliser condensate from a palm oil mill,
  f) waste from any oil clarification stage at a palm oil mill,
  g) waste from any centrifuge stage at a palm oil mill, or
  h) waste from any oil trap at a palm oil mill.

The above list is not intended to exhaust the possible sources of vegetation liquors derived from oil-bearing fruit and any other such sources not named explicitly, for example, olive flume wastewater, are meant to be included as input material for the invention. It will be clear that the input material is not restricted to pure fruit but also includes any ancillary vegetative matter collaterally processed with the fruit.

The present invention has as an object to provide improved treatments of vegetation liquors derived from oil-bearing fruit, for example from oil palm fruit, that is economically attractive. A further object of the present invention is to find new uses for, and better utilise the contents of, such vegetation liquors by recovering fractions containing valuable components including, but not limited to, flavonoids, phenolic acids and hydroxy acids. Another object of this invention is to put waste streams from oil-bearing fruit processing plants to more useful ends. Yet another object of the invention is to realise new and/or improved products through the use of aqueous substances derived from oil-bearing fruit, including but not limited to drinks, edible products, tonics, health supplements, antioxidant additives, cosmetics, soaps, shampoos, detergents, drugs or medicinal compositions. Concomitantly, an object of the invention is to reduce pollution by making feasible better treatments of waste streams from oil-bearing fruit processing plants.

There is herein disclosed, according to the invention, a method of obtaining a drink or an edible product or a tonic or a health supplement or an antioxidant additive or a cosmetic or a soap or a shampoo or a detergent or a drug or a medicinal product, characterised in that an aqueous fraction separated from vegetation liquor derived from oil-bearing fruit, said aqueous fraction having substantially no oleaginous parts, substantially no colloidal particles and substantially no undissolved solids, and said aqueous fraction containing, among other phytochemicals, flavonoids, phenolic acids and hydroxy acids, or a concentrate, a residue or an extract derived from said aqueous fraction, is combined in any way, form or proportion, to any other substance or substances.

According to this invention, a process is disclosed for extraction of phytochemicals from vegetation liquor derived from oil-bearing fruit characterised in that an aqueous fraction or a concentrated aqueous fraction or a residue containing said phytochemicals is separated and recovered from said vegetation liquor, said separation being adapted to remove, in one step or more, substantially all oleaginous parts, substantially all undissolved solids, substantially all colloidal particles and substantially all molecules above M Daltons in molecular weight, thereby giving said aqueous fraction containing solutes substantially all of which molecules are below M Daltons in molecular weight, where M, the molecular separation cut-off, is chosen to be less than 41,000 Daltons; some or substantially all of the water content of said aqueous fraction being removed to give said concentrated aqueous fraction or said residue Further according to the present invention, a process for extraction of phytochemicals from vegetation liquor derived from oil-bearing fruit comprises obtaining a colloidal fraction and an aqueous fraction from said vegetation liquor by the steps of putting said vegetation liquor in contact with a material that preferentially adsorbs or absorbs substantially all the oleaginous parts and filtering out substantially all the undissolved solids to give, as filtrate, an essentially colloidal aqueous substance, and separating said substance into two fractions by one or more membrane filtrations, giving as retentate, said colloidal fraction containing substantially all the colloidal particles and containing solutes substantially all of which molecules are above M Daltons in molecular weight, where M, the molecular separation cut-off, is chosen to be less than 41,000 Daltons; and giving as permeate, being substantially clear and containing solutes substantially all of which molecules are below M Daltons in molecular weight, said aqueous fraction.

Also according to his invention, a process for extraction of phytochemicals from vegetation liquor derived from oil-bearing fruit comprises obtaining an oleaginous fraction, a colloidal fraction and an aqueous fraction from said vegetation liquor by the steps of centrifuging said vegetation liquor to give a light phase, being essentially all the oleaginous parts, said light phase being recovered as said oleaginous fraction, a sediment phase containing substantially all the undissolved solids, and an aqueous phase which contains substantially all the colloidal particles and substantially all the solutes, said aqueous phase being recovered to give an essentially colloidal aqueous substance, or if necessary, filtered to remove out any remaining finer undissolved solids to give said essentially colloidal aqueous substance; and separating said substance into two fractions by one or more membrane filtrations, giving as retentate, said colloidal fraction containing substantially all the colloidal particles and containing solutes substantially all of which molecules are above M Daltons in molecular weight, where M, the molecular separation cut-off, is chosen to be less than 41,000 Daltons; and giving as permeate, being substantially clear and containing solutes substantially all of which molecules are below M Daltons in molecular weight, said aqueous fraction. An improvement is disclosed herein whereby the step of the process involving centrifugation of the vegetation liquor is conducted at a temperature below 13 degrees Celsius to better effect separation.

Alternatively, according to the present invention, a process for extraction of phytochemicals from vegetation liquor derived from oil-bearing fruit comprises obtaining an oleaginous fraction, a colloidal fraction and an aqueous fraction from said vegetation liquor by the steps of separating said vegetation liquor by one or more membrane filtrations into two parts, the retentate containing substantially all the oleaginous parts and substantially all the undissolved solids, said oleaginous retentate being filtered to remove substantially all the undissolved solids to give, as filtrate, said oleaginous fraction; and giving, as permeate, an aqueous fraction containing substantially all the colloidal particles and substantially all the solutes, this being an essentially colloidal aqueous substance; and separating said substance into two fractions by one or more membrane filtrations, giving as another retentate, said colloidal fraction containing substantially all the colloidal particles and containing solutes substantially all of which molecules are above M Daltons in molecular weight, where M, the molecular separation cut-off, is chosen to be less than 41,000 Daltons; and giving as another permeate, being substantially clear and containing solutes substantially all of which molecules are below M Daltons in molecular weight, said aqueous fraction.

In addition, according to the present invention, a process for extraction of phytochemicals from vegetation liquor derived from oil-bearing fruit comprises obtaining an oleaginous fraction, a colloidal fraction and an aqueous fraction from said vegetation liquor by the steps of filtering from said vegetation liquor substantially all of the undissolved solids contained in said vegetation liquor, and separating the filtrate so obtained into two parts by one or more membrane filtrations, giving as permeate, an aqueous substance containing substantially all the colloidal particles and substantially all the solutes; and, as retentate, giving said oleaginous fraction containing substantially all the oleaginous parts; and separating the permeate so obtained into two parts by one or more membrane fraction; giving as another retentate, said colloidal fraction containing substantially all the colloidal particles and containing solutes substantially all of which molecules are above M Daltons in molecular weight, where M, the molecular separation cut-off, is chosen to be less than 41,000 Daltons; and giving as another permeate, being substantially clear and containing solutes substantially all of which molecules are below M Daltons in molecular weight, said aqueous fraction.

According to the present invention, an improvement to the processes as described in the preceding paragraphs is disclosed which comprises the additional step of removing from said aqueous fraction, being the substantially clear permeate obtained as an end result of the processes of the preceding paragraphs, some part of or substantially all the water content to give either a concentrated aqueous fraction or a residue.

Another alternative according to the present invention is a process for extraction of phytochemicals from vegetation liquor derived from oil-bearing fruit which comprises obtaining a concentrated aqueous fraction or a residue from said vegetation liquor by the steps of separating said vegetation liquor into two parts by one or more membrane filtrations, the retentate containing substantially all the oleaginous parts, substantially all the colloidal particles and substantially all the undissolved solids; and giving as permeate, being substantially clear and containing solutes substantially all of which molecules are below M Daltons in molecular weight, an aqueous fraction, where M, the molecular separation cut-off, is chosen to be less than 41,000 Daltons; and removing from said aqueous fraction some or substantially all the water content therein to give either said concentrated aqueous fraction or said residue. Furthermore, according to this invention, an oleaginous fraction is recoverable from the retentate obtained in the first membrane filtration carried out in the process as described above in this paragraph.

There are herein disclosed, according to the present invention, substances that are products of the invented process as follows:
a) an aqueous fraction, being substantially clear and containing solutes substantially all of which molecules are below M Daltons in molecular weight, where M is chosen to be less than 41,000 Daltons,
b) a concentrated aqueous fraction, being said aqueous fraction with some part of the water content removed,
c) a residue, being said aqueous fraction or said concentrated aqueous fraction with substantially all the water content removed,
d) an extract rich in hydroxy acids or phenolic acids or flavonoids or any combination thereof, and
e) a dried extract rich in hydroxy acids or phenolic acids or flavonoids or any combination thereof.

The last two substances, namely said extract or said dried extract, according to the present invention, are obtained by a process which involves one or more steps of pH adjustment and solvent extraction upon either vegetation liquor derived from oil-bearing fruit or said aqueous fraction or said concentrated aqueous fraction or said residue reconstituted into an aqueous form.

There is herein disclosed, according to the present invention, a method of extracting phytochemicals by obtaining an aqueous fraction containing, among other phytochemicals, flavonoids, phenolic acids and hydroxy acids, or obtaining a concentrated aqueous fraction containing, among other phytochemicals, flavonoids, phenolic acids and hydroxy acids, or obtaining a residue containing, among other phytochemicals, flavonoids, phenolic acids and hydroxy acids, or obtaining an extract rich in hydroxy acids or phenolic acids or flavonoids or any combination thereof, or obtaining a dried extract rich in hydroxy acids or phenolic acids or flavonoids or any combination thereof, through the application of the invented process to vegetation liquor derived from oil-bearing fruit.

According to the present invention, the invented substances disclosed may be used to make, or are contained in, drinks, edible products, tonics, health supplements, antioxidant additives, cosmetics, soaps, shampoos, detergents, drugs or medicinal products. It is clear, according to this invention, that products may be produced using or containing, in any way, form or proportion, a fraction extracted from vegetation liquor derived from oil-bearing fruit, in particular from palm oil null effluent or from concentrated palm oil mill effluent, said fraction having substantially no oleaginous parts, substantially no colloidal particles and substantially no undissolved solids, and said fraction containing, among other phytochemicals, flavonoids, phenolic acids and hydroxy acids.

Low grade oil may be recovered for sale from the oleaginous fraction, and the colloidal fraction may be sold as animal feed, as animal food supplement or as substrate for microbial growth. The water from the invented process is substantially pure and is recyclable. The invention realises new products which will enhance effluent treatment economics. The invention further provides an apparatus, or a combination of devices, for extraction of phytochemicals from vegetation liquor derived from oil-bearing fruit characterised in that means are provided in said apparatus, or in said combination of devices, to perform the processes as described herein.

EXAMPLES

Specific embodiments of the invention will now be described by way of example only. While the embodiments here deal wit vegetation liquor derived from oil palm, it is intended that the invention will find wider application to other sources of vegetation liquor derived from oil-bearing it.

As a preliminary example, vegetation liquor is derived from fifteen oil palm fruitlets by autoclaving at 120 degrees Celsius at a gauge pressure of 103421 Pascals (15 psig) for 15 minutes following addition of 5 millilitres of water. The liquor so derived is collected and filtered through a Whatman number 4 filter paper. The filtrate is then transferred into a Centriprep 10 (A icon) system and is centrifuged to give a permeate containing solutes of molecular weight less than 10,000 Daltons, this providing the aqueous fraction from the vegetation liquor, the presence of the phytochemicals being confirmed by analysis (details below). A sample of the aqueous fraction is used to recover an extract containing hydroxy acids and phenolic acids and flavonoids by extracting with ethyl acetate, first at a neutral pH of 7 achieved by adding sodium hydroxide, and subsequently at a pH of 2 achieved by adding hydrochloric acid, the presence of the hydroxy acids and phenolic acids and flavonoids being confirmed by analysis (see below for details).

In a second example, vegetation liquor is derived from an oil palm fruit bunch, weighing approximately 18 kilograms, by autoclaving at 120 degrees Celsius at a gauge pressure of 117211 Pascals (17 psig) for 40 minutes. The liquor so derived is collected and filtered through a Whatman number 4 filter paper. The filtrate is then collected and is circulated through a pumped ultrafiltration device with a hollow fibre cartridge with nominal molecular weight cut-off of 10,000 Daltons to give a permeate containing solutes of molecular weight less than 10,000 Daltons, this providing the aqueous fraction from the vegetation liquor, the presence of the phytochemicals being confirmed by analysis (details below). A sample of the aqueous fraction is used to recover an extract containing hydroxy acids and phenolic acids and flavonoids by extracting with ethyl acetate, first at a neutral pH of 7 achieved by adding sodium hydroxide, and subsequently at a pH of 2 achieved by adding hydrochloric acid, the presence of the hydroxy acids and phenolic acids and flavonoids being confirmed by analysis (see below for details).

As a third example, vegetation liquor in the form of hot steriliser condensate is collected immediately on discharge from the horizontal sterilisers at a palm oil mill. After a short transport time to the laboratory, this condensate is then cooled to between 8 and 10 degrees Celsius before centrifuging in a refrigerated centrifuge at 10 degrees Celsius at 5000 g for 30 minutes. The light phase so generated is then skimmed off to give an oleaginous fraction. The middle aqueous phase is then decanted, thereby separating this phase from the now-pelleted solids, to give a colloidal aqueous substance. This substance is then arranged to be circulated through a pumped ultrafiltration device with a hollow fibre cartridge with nominal molecular weight cut-off of 10,000 Daltons to give a permeate containing solutes of molecular weight less than 10,000 Daltons, this providing the aqueous fraction from the vegetation liquor, the presence of the phytochemicals being confirmed by analysis (details below). A sample of the aqueous fraction is used to recover an extract containing hydroxy acids and phenolic acids and flavonoids by extracting with ethyl acetate, first at a neutral pH of 7 achieved by adding sodium hydroxide, and subsequently at a pH of 2 achieved by adding hydrochloric acid, the presence of the hydroxy acids and phenolic acids and flavonoids being confirmed by analysis (see below for details).

In a fourth example, the same process as in the third example above is carried out with the difference that, in the ultrafiltration device, the nominal molecular cut-off of the hollow fibre cartridge is 30,000 Daltons. The permeate therefore contains solutes of molecular weight less than 30,000 Daltons, this providing the aqueous fraction from the vegetation liquor, the presence of the phytochemicals being confirmed by analysis (details below). As before, a sample of the aqueous fraction is used to recover an extract containing hydroxy acids and phenolic acids and flavonoids by extracting with ethyl acetate, first at a neutral pH of 7 achieved by adding sodium hydroxide, and subsequently at a pH of 2 achieved by adding hydrochloric acid, the presence of the hydroxy acids and phenolic acids and flavonoids being confirmed by analysis (see below for details).

As a fifth example, vegetation liquor is collected immediately on discharge from the sludge centrifuge at a palm oil mill, and after a short transport time to the laboratory, is then cooled to between 8 and 10 degrees Celsius before centrifuging in a refrigerated centrifuge at 10 degrees Celsius at 5000 g for 30 minutes. The light phase so generated is then skimmed off to give an oleaginous fraction. The middle aqueous phase is then decanted, thereby separating this phase from the now-pelleted solids, to give a colloidal aqueous substance. This substance is then circulated through a pumped ultrafiltration device with a hollow fibre cartridge with nominal molecular weight cut-off of 10,000 Daltons to give a permeate containing solutes of molecular weight less than 10,000 Daltons, this providing the aqueous fraction from the vegetation liquor, the presence of the phytochemicals being confirmed by analysis (details below). A sample of the aqueous fraction is used to recover an extract containing hydroxy acids and phenolic acids and flavonoids by extracting with ethyl acetate, first at a neutral pH of 7 achieved by adding sodium hydroxide, and subsequently at a pH of 2 achieved by adding hydrochloric acid, the presence of the hydroxy acids and phenolic acids and flavonoids being confirmed by analysis (see below for details).

In a sixth example, the same process as in the fifth example above is carried out with the difference that, in the ultrafiltration device, the nominal molecular cut-off of the hollow fibre cartridge is 30,000 Daltons. The permeate therefore contains solutes of molecular weight less than 30,000 Daltons, this providing the aqueous fraction from the vegetation liquor, the presence of the phytochemicals being confirmed by analysis (details below). As before, a sample of the aqueous fraction is used to recover an extract containing hydroxy acids and phenolic acids and flavonoids by extracting with ethyl acetate, first at a neutral pH of 7 achieved by adding sodium hydroxide, and subsequently at a pH of 2 achieved by adding hydrochloric acid, the presence of the hydroxy acids and phenolic acids and flavonoids being confirmed by analysis (see below for details).

The oleaginous fraction is found to comprise low grade crude palm oil with about a quarter of its content as free fatty acids. The colloidal fraction is found to be proteinaceous. The aqueous fraction is found to contain essential minerals (iron, phosphorus, calcium, magnesium), sugars (among which are glucose, fructose, sucrose), vitamins (among which are vitamin C, the B-complex vitamins, folic acid), flavonoids (among which are catechin, catechin gallate, epicatechin, epigallocatechin, epigallocatechin gallate, epicatechin gallate, quercetin), phenolic acids (among which are caffeic acid, protocatechuic acid, vanillic acid, ferulic acid, syringic acid, chlorogenic acid, gallic acid, tannic acid, coumaric acid) and hydroxy acids (among which are citric acid, ascorbic acid, lactic acid, glycolic acid, fumaric acid, tartaric acid, salicyclic acid). Where the aqueous fraction is obtained using the membrane with the higher (30,000 Dalton) molecular weight cut-off, the solutes contain more proteins and other filtrates, which could reduce the purity depending on the eventual application. The residue obtained by freeze drying the aqueous fraction is found to contain an average of about 40,000 parts per million of flavonoids and other phenolic compounds, and antioxidant activity is indicated. The extract is found to contain hydroxy acids (among which are citric acid, ascorbic acid, lactic acid, glycolic acid, fumaric acid, tartaric acid, salicyclic acid), phenolic acids (among which are caffeic acid, protocatechuic acid, vanillic acid, ferulic acid, syringic acid, chlorogenic acid, gallic acid, tannic acid, coumaric acid) and flavonoids (among which are catechin, catechin gallate, epicatechin, epigallocatechin, epigallocatechin gallate, epicatechin gallate, quercetin).

As a seventh example, fresh palm oil mill effluent is filtered to remove undissolved solids and the filtrate is subject to membrane filtration using the Membrex Ultrafilic system with a molecular weight cut-off of 100,000 Daltons. This gives the oleaginous fraction as retentate and, as permeate, gives an essentially colloidal aqueous substance which is subject to another membrane filtration with molecular weight cut-off of 10,000 Daltons. This gives the colloidal fraction as another retentate and, as another permeate, gives the aqueous fraction containing, among other phytochemicals, flavonoids, phenolic acids and hydroxy acids. This aqueous fraction is concentrated or dried and the water so obtained is substantially pure.

While examples of the invention have been described in detail, it should be apparent that many modifications and variations thereto are possible all of which fall within the true spirit and scope of the invention.

What is claimed is:

1. A process for extraction of phytochemicals from vegetation liquor derived from oil bearing fruit comprising:
    filtering a colloidal aqueous filtrate obtained from said vegetation liquor with a membrane filter, wherein said membrane filter removes molecules above 41,000 Daltons in molecular weight and allows molecules 41,000 Daltons or less to pass through;
    wherein the membrane filtration yields an aqueous permeate comprising phytochemicals; and
    wherein the colloidal aqueous filtrate is obtained from said vegetation liquor by the following pre-filtration treatment:
        a) contacting said vegetation liquor with a material that preferentially adsorbs or absorbs substantially all oleaginous parts, and thereafter
        b) filtering said vegetation liquor to yield an oleaginous retentate and said colloidal aqueous filtrate.

2. The process of claim 1, wherein the vegetation liquor is subjected to a pre-filtration treatment of filtering out substantially all solids therefrom, prior to the membrane filtration thereof.

3. The process of claim 1, further comprising removing part of the water content from the aqueous permeate to give a concentrated aqueous fraction, or a residue.

4. The process of claim 3, wherein substantially all of the water content is removed from the aqueous permeate to give a concentrated aqueous fraction, or a residue.

5. An aqueous fraction containing phytochemicals obtained by the process of claim 1.

6. The aqueous fraction of claim 5, which has been concentrated by removing some of the water content.

7. A residue containing phytochemicals produced by removing substantially all of the water content from the aqueous fraction obtained by the process of claim 1.

8. The process of claim 1, wherein the vegetation liquor is derived from olive flume wastewater.

9. The process of claim 1, wherein said aqueous permeate is substantially free of oleaginous parts, colloidal substances, and solids.

10. The process of claim 1, wherein said membrane filter removes molecules above 30,000 Daltons in molecular weight and allows molecules 30,000 Daltons or less to pass through.

11. The process of claim 1, wherein said membrane filter removes molecules above 10,000 Daltons in molecular weight and allows molecules 10,000 Daltons or less to pass through.

12. The process of claim 1, wherein said membrane filter is a part of a Centriprep system.

13. The process of claim 1, wherein said membrane filter is a hollow fibre cartridge.

14. A process for obtaining an oil bearing fruit extract comprising hydroxy acids, phenolic acids or flavonoids from vegetation liquor obtained from the oil bearing fruit, said process comprising:
 (a) filtering said vegetation liquor with a membrane filter, wherein said membrane filter removes molecules above 41,000 Daltons in molecular weight and allows molecules 41,000 Daltons or less to pass through with the permeate;
 (b) adjusting the pH of the permeate of step (a) to effect separation of hydroxy acids, phenolic acids or flavonoids or any combination thereof into either an aqueous phase or a solvent phase; and
 (c) recovering the phase containing the hydroxy acids, phenolic acids or flavonoids or any combination thereof, thereby obtaining the extract.

15. The process of claim 14, wherein the vegetation liquor is concentrated or reconstituted from a residue prior to step (a).

16. An extract comprising hydroxy acids, phenolic acids or flavonoids obtained by the process of claim 14.

17. The extract of claim 16, which has been dried by removing substantially all of the water or substantially all of the solvent.

* * * * *

UNITED STATES PATENT AND TRADEMARK OFFICE
CERTIFICATE OF CORRECTION

PATENT NO. : 8,309,145 B2
APPLICATION NO. : 12/126736
DATED : November 13, 2012
INVENTOR(S) : Ravigadevi Sambanthamurthi Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 296 days.

Signed and Sealed this
Seventh Day of May, 2013

Teresa Stanek Rea
*Acting Director of the United States Patent and Trademark Office*